United States Patent
Johnson et al.

[11] Patent Number: 5,954,485
[45] Date of Patent: Sep. 21, 1999

[54] FREE-FLOW PROTECTION DEVICES AND METHODS

[75] Inventors: Jay Gregory Johnson, Maple Plain; Jia Hu, New Brighton, both of Minn.

[73] Assignee: SIMS Deltec, Inc., St. Paul, Minn.

[21] Appl. No.: 08/696,532

[22] Filed: Aug. 14, 1996

[51] Int. Cl.[6] .................................................... F04B 43/08
[52] U.S. Cl. .......................................... 417/474; 604/153
[58] Field of Search .................................. 417/474, 417, 417/437.2; 604/153, 131, 151

[56] References Cited

U.S. PATENT DOCUMENTS

| | | |
|---|---|---|
| D. 376,848 | 12/1996 | Zeilig et al. . |
| 3,402,673 | 9/1968 | Ballentine et al. . |
| 3,559,644 | 2/1971 | Stoft et al. . |
| 3,620,650 | 11/1971 | Shaw . |
| 4,025,241 | 5/1977 | Clemens . |
| 4,187,057 | 2/1980 | Xanthopoulos . |
| 4,236,880 | 12/1980 | Archibald . |
| 4,394,862 | 7/1983 | Shim . |
| 4,482,347 | 11/1984 | Borsanyi . |
| 4,535,820 | 8/1985 | Raines . |
| 4,559,038 | 12/1985 | Berg et al. . |
| 4,565,542 | 1/1986 | Berg . |
| 4,585,441 | 4/1986 | Archibald . |
| 4,650,469 | 3/1987 | Berg et al. . |
| 4,657,486 | 4/1987 | Stempfle et al. . |
| 4,671,792 | 6/1987 | Borsanyi . |
| 4,689,043 | 8/1987 | Bisha . |
| 4,925,152 | 5/1990 | Huber . |
| 4,944,485 | 7/1990 | Daoud et al. . |
| 5,017,059 | 5/1991 | Davis . |
| 5,017,192 | 5/1991 | Dodge et al. . |
| 5,074,756 | 12/1991 | Davis . |
| 5,078,683 | 1/1992 | Sancoff et al. . |
| 5,096,385 | 3/1992 | Georgi et al. . |
| 5,096,393 | 3/1992 | Van Steenderen et al. . |
| 5,165,874 | 11/1992 | Sancoff et al. . |
| 5,213,483 | 5/1993 | Flaherty et al. . |
| 5,226,886 | 7/1993 | Skakoon et al. . |
| 5,254,086 | 10/1993 | Palmer et al. . |
| 5,257,978 | 11/1993 | Haber et al. ........................ 604/153 X |
| 5,308,333 | 5/1994 | Skakoon . |
| 5,336,174 | 8/1994 | Daoud et al. . |
| 5,336,190 | 8/1994 | Moss et al. . |
| 5,397,222 | 3/1995 | Moss et al. . |
| 5,401,256 | 3/1995 | Stone et al. . |
| 5,425,173 | 6/1995 | Moss et al. . |
| 5,437,642 | 8/1995 | Thill et al. .......................... 417/474 X |
| 5,453,098 | 9/1995 | Botts et al. . |
| 5,482,446 | 1/1996 | Williamson et al. ............... 604/153 X |
| 5,531,697 | 7/1996 | Olsen et al. . |
| 5,564,915 | 10/1996 | Johnson . |
| 5,630,710 | 5/1997 | Tune et al. . |

FOREIGN PATENT DOCUMENTS

| | | |
|---|---|---|
| 0 510 881 A2 | 10/1992 | European Pat. Off. . |
| 0 569 030 A1 | 11/1993 | European Pat. Off. . |
| 41 26 088 C1 | 1/1993 | Germany . |
| WO 95/16480 | 6/1992 | WIPO . |
| WO 93/10853 | 6/1993 | WIPO . |
| WO 96/27402 | 9/1996 | WIPO . |
| WO 97/02059 | 1/1997 | WIPO . |

OTHER PUBLICATIONS

Photographs of a pump product by Patient Solutions, Inc., Med–Mate™, Model 1100, pp. A1–A5.

Photographs of a pump product by Block Medical, Inc., a Hillenbrand Industry, Verifuse® Model No. B001500, pp. B1–B3.

Photographs of a pump product by Medfusion, Inc., a Medex, Inc. Company, Infu–Med™, WalkMed™ 440 PIC, pp. C1–C2.

(List continued on next page.)

*Primary Examiner*—Ismael Izaguirre
*Attorney, Agent, or Firm*—Merchant & Gould P.C.

[57] ABSTRACT

The present invention describes a free-flow protection device. A pump and tube are provided where the pump affects the flow of fluid through the tube. The device occludes the tube when the tube becomes disengaged from the pump. The device may be internal or external to the tube. The tube may attach to the pump with a pressure plate.

11 Claims, 13 Drawing Sheets

OTHER PUBLICATIONS

Photographs of a pump product by C.R. Bard, Inc., Bard Medsystems Division, pp. D1–D3.

Photographs of a pump product by Pharmacia Deltec, Inc., pp. E1–E2.

Photographs of a pump product by AVI, Inc., AVI Guardian™ MICRO 110, pp. F1–F4.

Photographs of a pump product by Abbott Laboratories, Abbott/Shaw LifeCare®Pump Model 3, pp. G1–G3.

Bard MedSystems Division, C.R. Bard, Inc., Bard® Ambulatory PCA Pump Operator's Manual, 43 pages, dated Apr. 1990.

AVI, Inc. literature entitled "The AVI Advantage,", 2 pages, dated 1983.

AVI, Inc. literature, entitled "Bridging the Gap," 6 pages, dated Apr. 22, 1983.

Abbott Laboratories Hospital Products Dvision literature, entitled "The Blue Line System LifeCare®," 16 pages, dated Jul., 1990.

Abbott Laboratories Hospital Products Dvision literature, entitled "LifeCare® Electronic Flow Control Systems Catalog," 34 pages, dated May, 1985.

Patient Solutions, Inc. literature for MedMate™ 1100, 2 pages.

Patient Solutions, Inc. Directions for Use, MedMate™ model 1100, 61 pages.

Block Medical, Inc. literature for VERIFUSE System, 1 page, dated Nov. 1990.

Medfusion, Inc. Operations Manual for Medfusion WALK-MED™ Ambulatory Infusion Pump, 92 pages, dated Apr., 1990.

Medex Ambulatory Infusion Systems literature, entitled "WalkMed Pump Disposable Products," 2 pages, dated 1992.

Medex Ambulatory Infusion Systems literature, entitled "WalkMed PCA," 2 pages, dated 1993.

Bard Ambulatory PCA Pump literature, 2 pages, dated Jun. 1990.

Bard MedSystems Division, C.R. Bard, Inc., Quick Reference Guide, 2 pages, dated Feb. 1992.

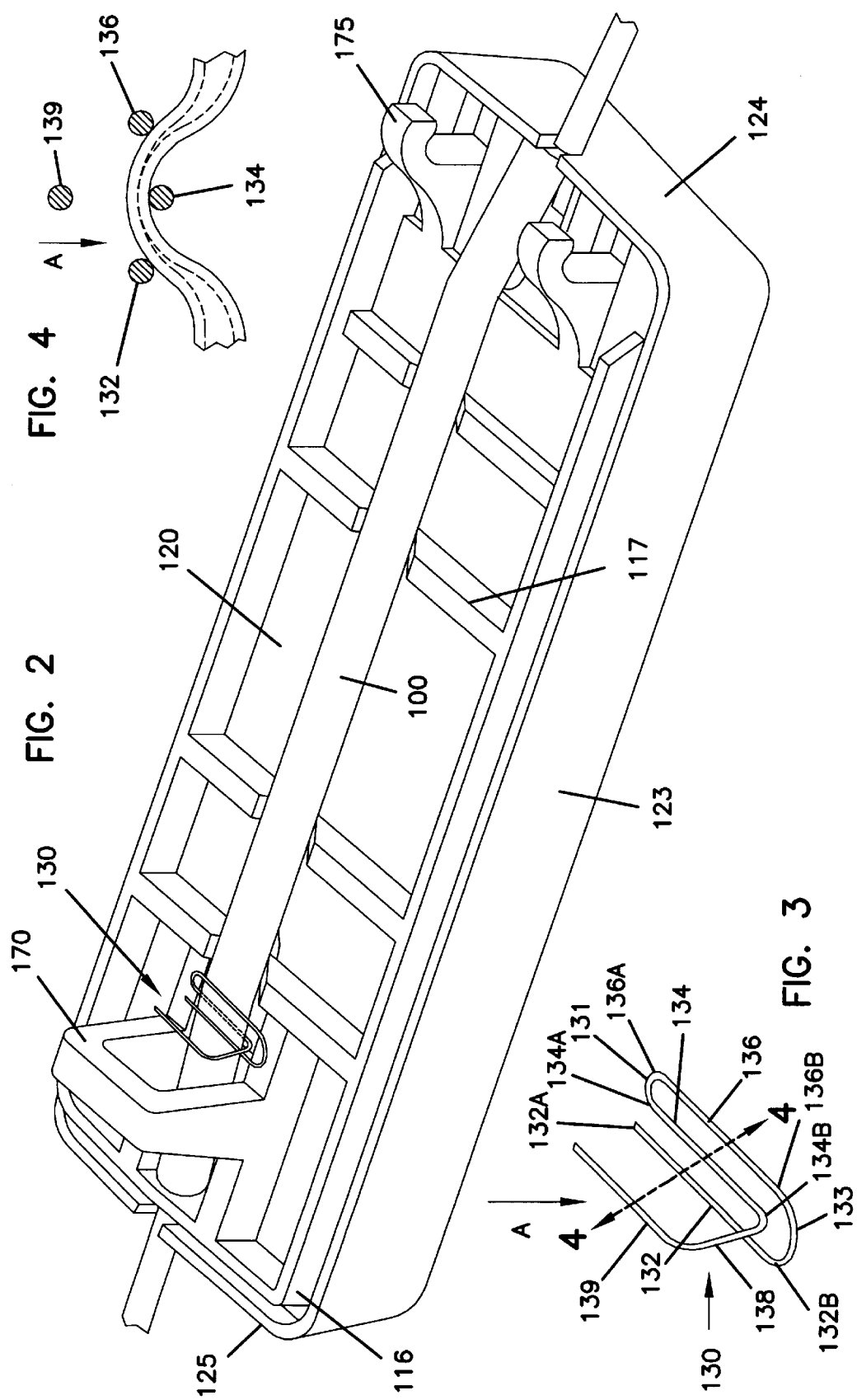

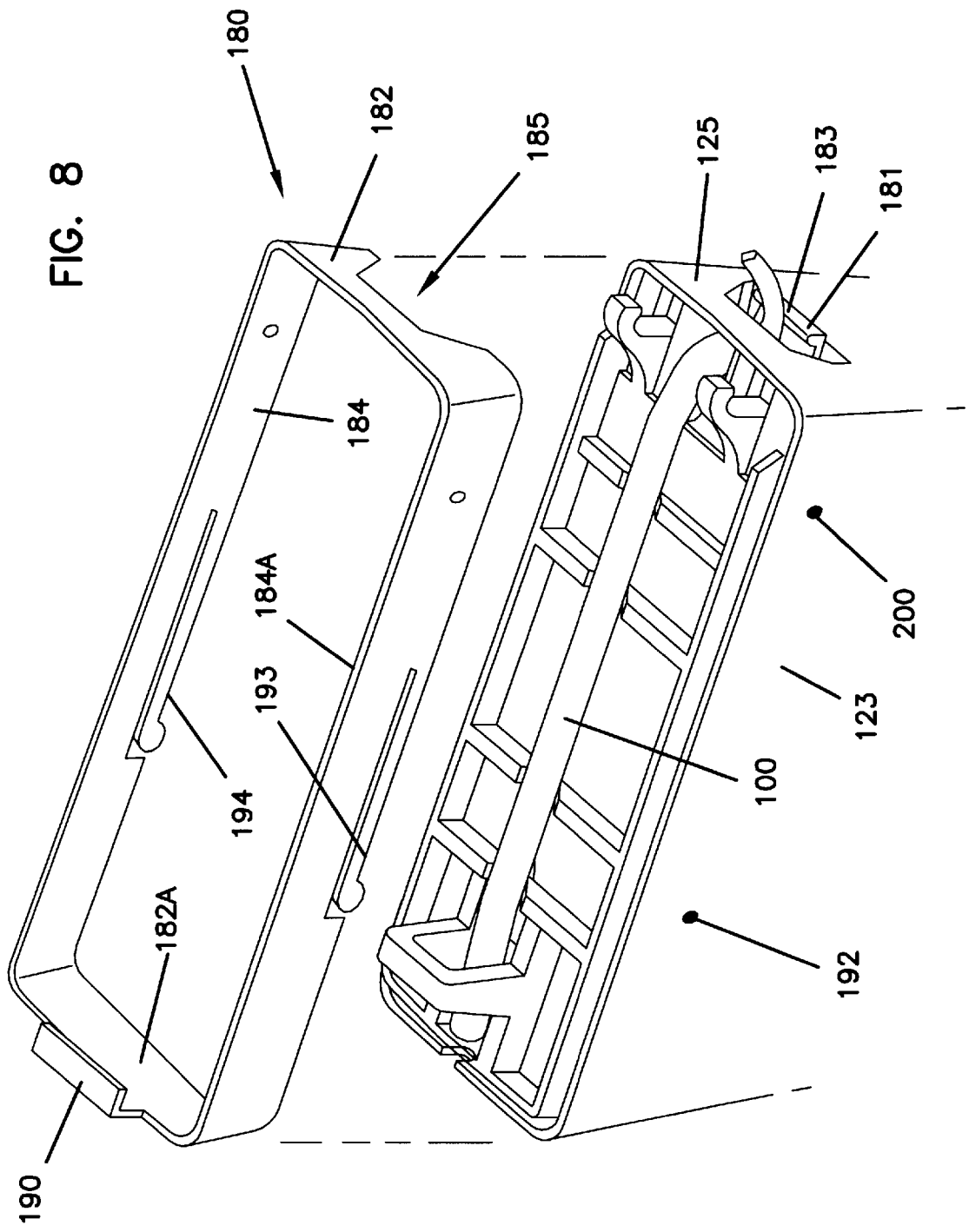

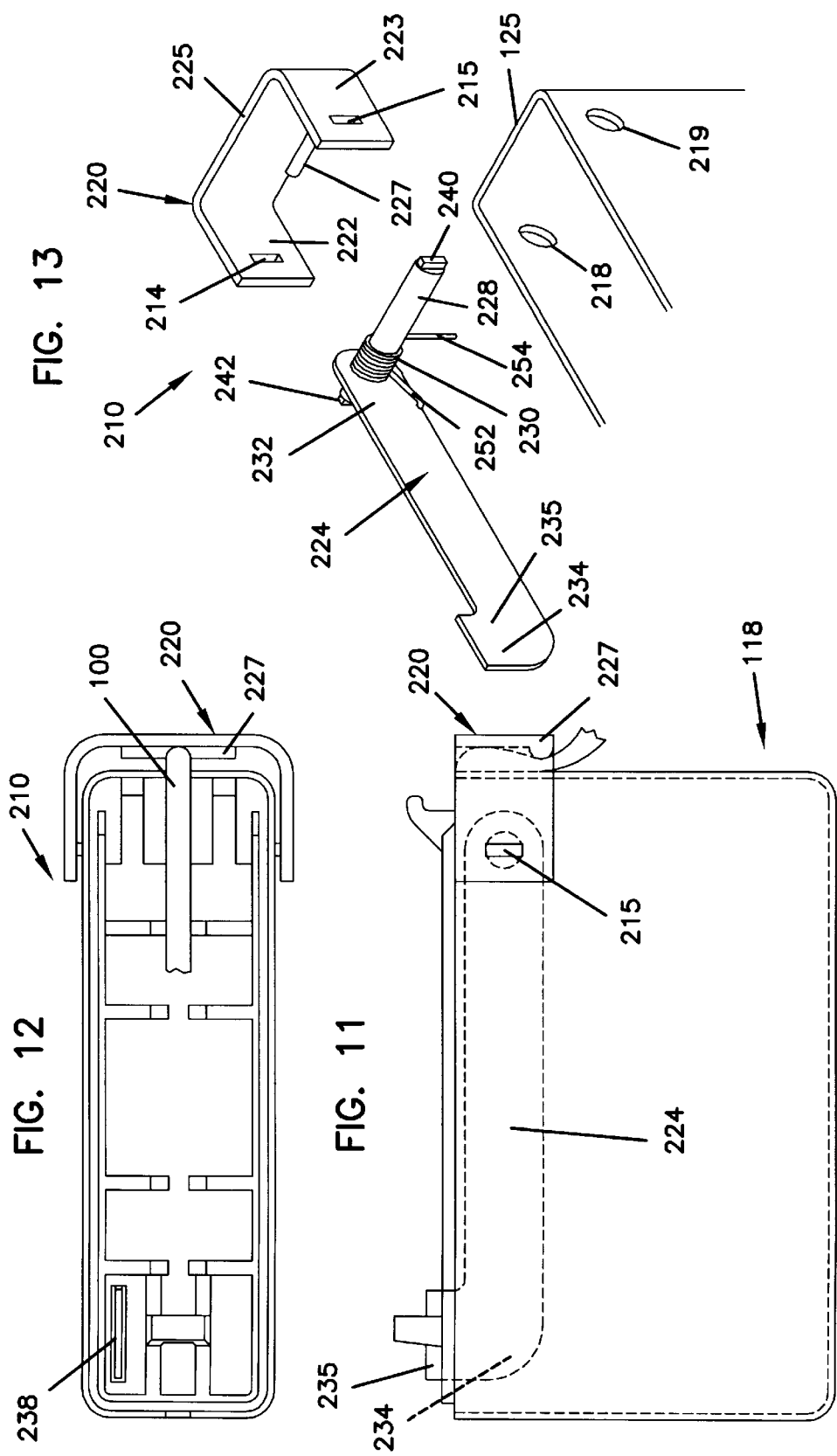

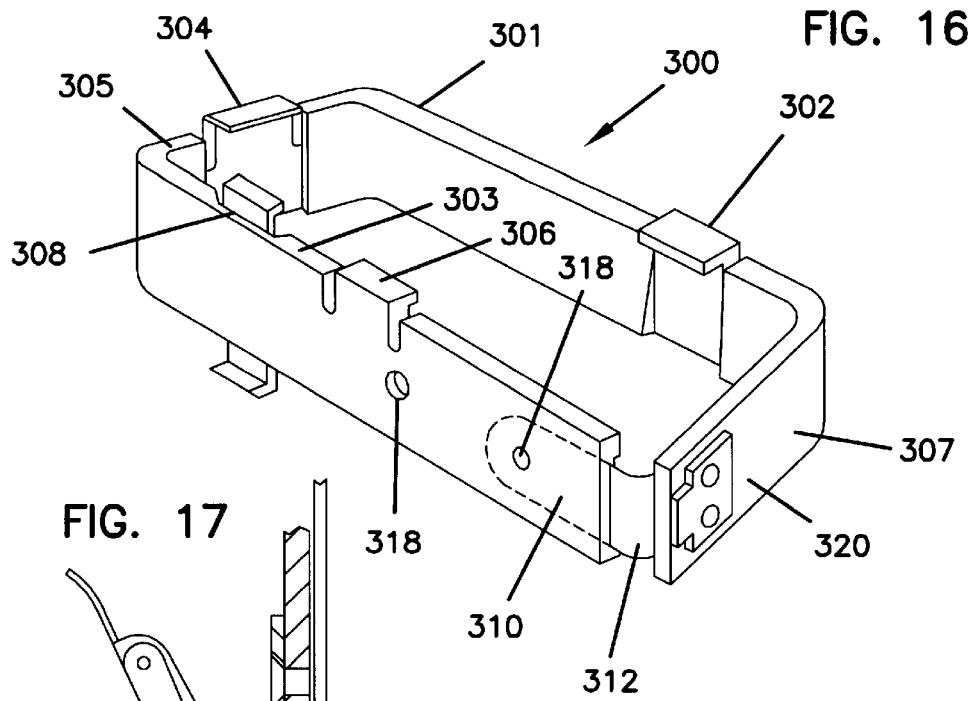
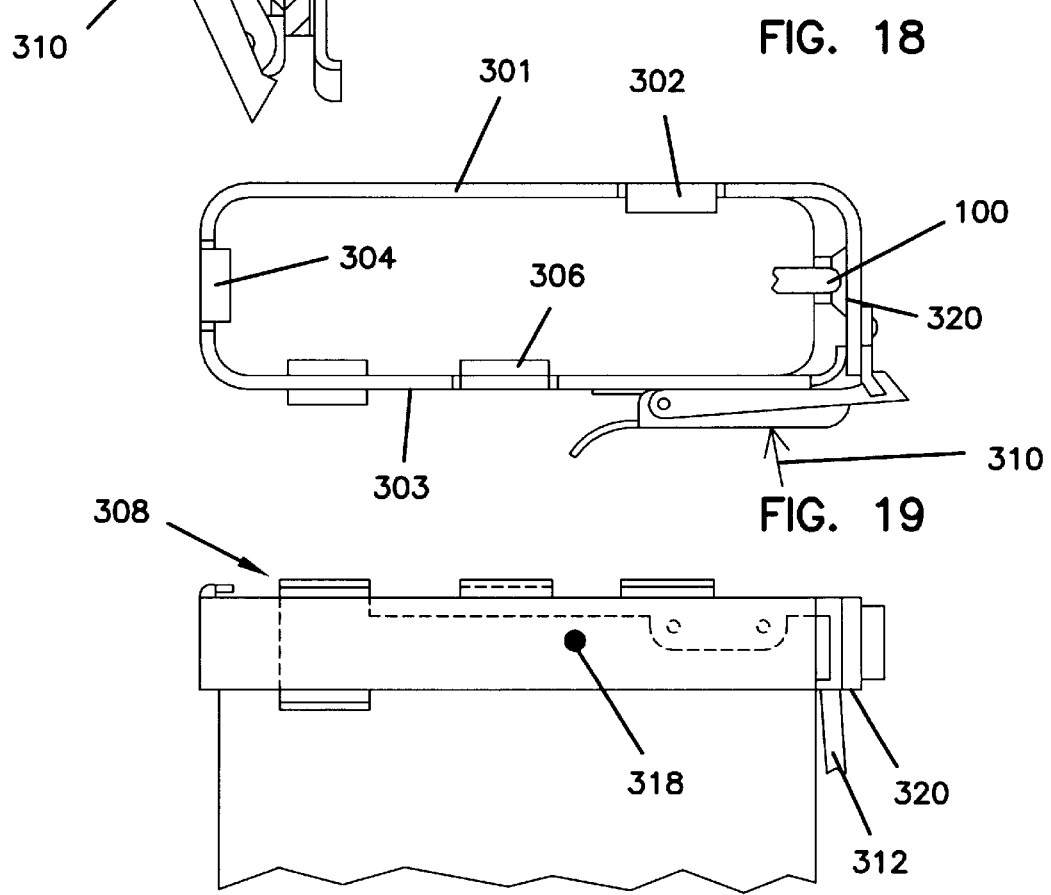

FREE-FLOW PROTECTION DEVICES AND METHODS

BACKGROUND OF THE INVENTION

The present invention relates to free-flow protection devices and methods for use with intravenous infusion pumps. The free-flow protection devices are operative in occluding a pumping tube to prevent free-flow of a medicant to a patient.

Intravenous infusion pumps are used to deliver a fluid which may include medicants or nutrients to a patient through a tube set. The tube set, commonly referred to as an administration set, typically includes a tube connected between a source of fluid and a tube which passes into the patient. Infusion pumps operate to either force fluid from the source through the tube and into the catheter or control the flow of fluid through the tube into the catheter. Infusion pumps may include peristaltic pumps, roller pumps or expulsor type pumps. Examples of infusion pumps are illustrated in U.S. Pat. No. 4,559,038 to Berg, U.S. Pat. No. 5,096,385 to Georgi and U.S. Pat. No. 4,394,862 to Shim.

These infusion pumps effect the movement of fluid through the tube by selectively occluding portions of the tube by depressing a valve or finger against the tube. For example, U.S. Pat. No. 5,056,385 to Georgi illustrates a peristaltic pump in which the tube is positioned between a plurality of fingers and a pressure plate. The source of fluid is positioned in a bag remote from the pump. The fingers of the pump selectively engage the tube against the pressure plate in a peristaltic fashion to force fluid through the tube. The fingers of the Shim patent may also be used to control the flow of fluid through the tube.

The pump disclosed in U.S. Pat. No. 4,559,038 is an expulsor pump which effects the delivery of fluid from a reservoir to the patient. In the '038 patent, the fluid is in a bag held in a container, or cassette, immediately adjacent to the pump. The pump effects the amount of fluid to the patient by physically occluding the tube against a pressure plate which restricts the volume of fluid allowed to flow to the patient. The pump includes a pump mechanism which engages the tube with an inlet valve, an outlet valve and a central expulsor which squeezes the tube against the pressure plate associated with the cassette to effect pumping of the fluid. The pump of the '038 patent has also been used with a pressure plate not having a self contained fluid reservoir, where the fluid is in a bag positioned remote from the pump.

Free-flow is the condition where fluid flows freely from the source of fluid through the t-be and into the patient. Caregivers attempt to avoid frees-flow when administering fluids with an infusion pump. Fluid flow may be a result of a pressure head associated with the administration set which is greater than the blood pressure of the patient. The free-flow condition will continue until the pressure head of the administration set equalizes with the blood pressure of the patient. A free-flow condition may cause significant harm to the patient including harm which is the direct result of over medicating the patient.

Typically, free-flow will not occur when the tube set is attached to the infusion pump because the roller, at least one valve, or finger of the infusion pump always occludes the tube at any given time. When the tube is engaged by the pump it is temporarily occluded and fluid will not flow. However, if the tube disengages from the pump, the tube will no longer be occluded by the pump and a free-flow condition may exist.

Free-flow can be prevented by providing a valve positioned in-line with the administration set. One such valve is described in U.S. Pat. No. 4,535,820 to Raines. Raines describes an in-line pressure valve which requires a predetermined crack pressure or differential pressure, such as 1.5 psi, to open the valve. In an administration tube set, the infusion pump will create a pressure increase within the tube above the crack pressure of the valve, thereby opening the valve and allowing fluid to be delivered to the patient.

However, the valve of Raines does not fully solve the problem of unwanted free-flow. For example, situations may exist when the pressure head provided by the source of fluid may be great enough to open the valve of Raines, resulting in unnecessarily delivering fluid to the patient. Further, the addition of the valve of Raines in an administration set may affect the volume of fluid delivered to a patient in a normal fluid delivery cycle. Because of these and other problems within the prior art a need has arisen to provide devices and methods which guarantee that free-flow will not occur when the tube becomes disengaged from the infusion pump.

SUMMARY OF THE INVENTION

The present invention provides a cassette for attachment to a pump where the cassette includes a pressure plate and a tube attached thereto. The pressure plate is selectively attachable to the pump so that when the tube and pressure plate are attached to the pump the pump effects movement of fluid through the tube. The cassette further includes a free-flow protection device responsive to the pressure plate being engaged to the pump to move the free-flow protection device from a tube occluding state to a free-flow state.

The present invention also provides a free-flow protection device for occluding a tube when the tube disengages from a pump. The tube is connectable to the pump by a pressure plate so that the pump moves fluid through the tube. The free-flow protection device includes a lever deflectable between a first position and a second position such that when the pressure plate is engaged to the pump the lever is in the first position and when the pressure plate is disengaged from the pump the lever is in the second position. The device further includes a clamping portion movable between an occluding position and a free-flow position, the clamping portion connected to the lever so that when the lever is in its first position the clamping portion is in its free-flow position and when the lever is in its second position the clamping portion is its occluding position.

The present invention also provides a free-flow protection device positioned within the lumen of the tube which allows free-flow when the tube is engaged to the pump, and occludes the tube when the tube disengages from the pump. The device includes a valve which selectively occludes the tube by providing at least two semi-circular sections which occlude the tube when the tube is not compressed, and which deflect from one another to from an aperture when the tube is compressed.

The present invention further provides a method of pumping a fluid through a tube including providing a pump and a pressure plate, and placing the tube between the pump and the pressure plate so that the pump operates to move fluid through the tube. When the tube is attached to the pump, the free-flow protection device permits fluid to flow through the tube. The method provides for occluding the tube when the tube disengages from the pump.

BRIEF DESCRIPTION OF THE DRAWINGS

FIG. 2 is perspective view of a pressure plate and a tube including a free-flow protection device according to a first preferred embodiment of the present invention;

FIG. 3 is an enlarged perspective view of the free-flow protection device of FIG. 1;

FIG. 4 is a cross-sectional view of the free-flow protection device of FIG. 3 showing the tube in an occluded state;

FIG. 8 is a perspective view of a free-flow protection device and a pressure plate according to a third preferred embodiment;

FIG. 11 is a side view of a free-flow protection device and pressure plate according to a forth preferred embodiment;

FIG. 12 is a top view of the free-flow protection device and the pressure plate of FIG. 11;

FIG. 13 is an exploded view of the free-flow protection device of FIGS. 11 and 12;

FIG. 16 is a perspective view of a free-flow protection device according to a sixth preferred embodiment;

FIG. 17 is a top view of an attachment clamp of the free-flow protection device of FIG. 16;

FIG. 18 is a top view of the free-flow protection device of FIG. 16, including a tube;

FIG. 19 is a side view of the free-flow protection device of FIG. 16 attached to a pressure plate and a cassette;

DETAILED DESCRIPTION OF THE PREFERRED EMBODIMENTS

The present invention addresses the problem of free-flow of fluid through a tube by occluding the tube if the tube disengages from an infusion pump. The device can be positioned within the lumen of the tube or outside of the tube. The device may be positioned adjacent to a pressure plate which may be associated with a cassette and occludes the tube when the pressure plate become disengaged from the pump.

Figure 1:
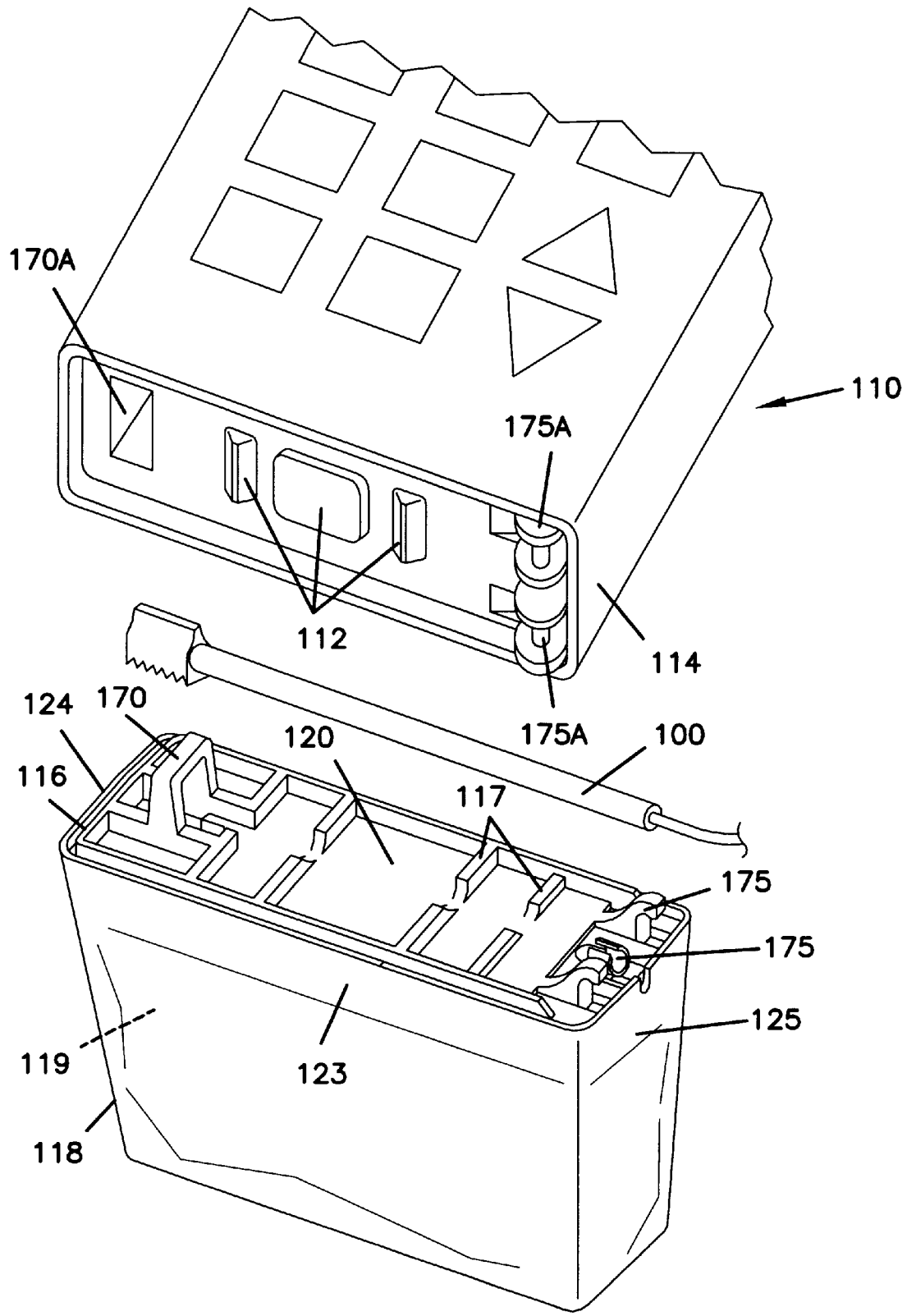
FIG. 1 is a perspective view of a pump, a tube, a pressure plate and a cassette of an infusion pump system where free-flow protection is desired.
Figure 1A:
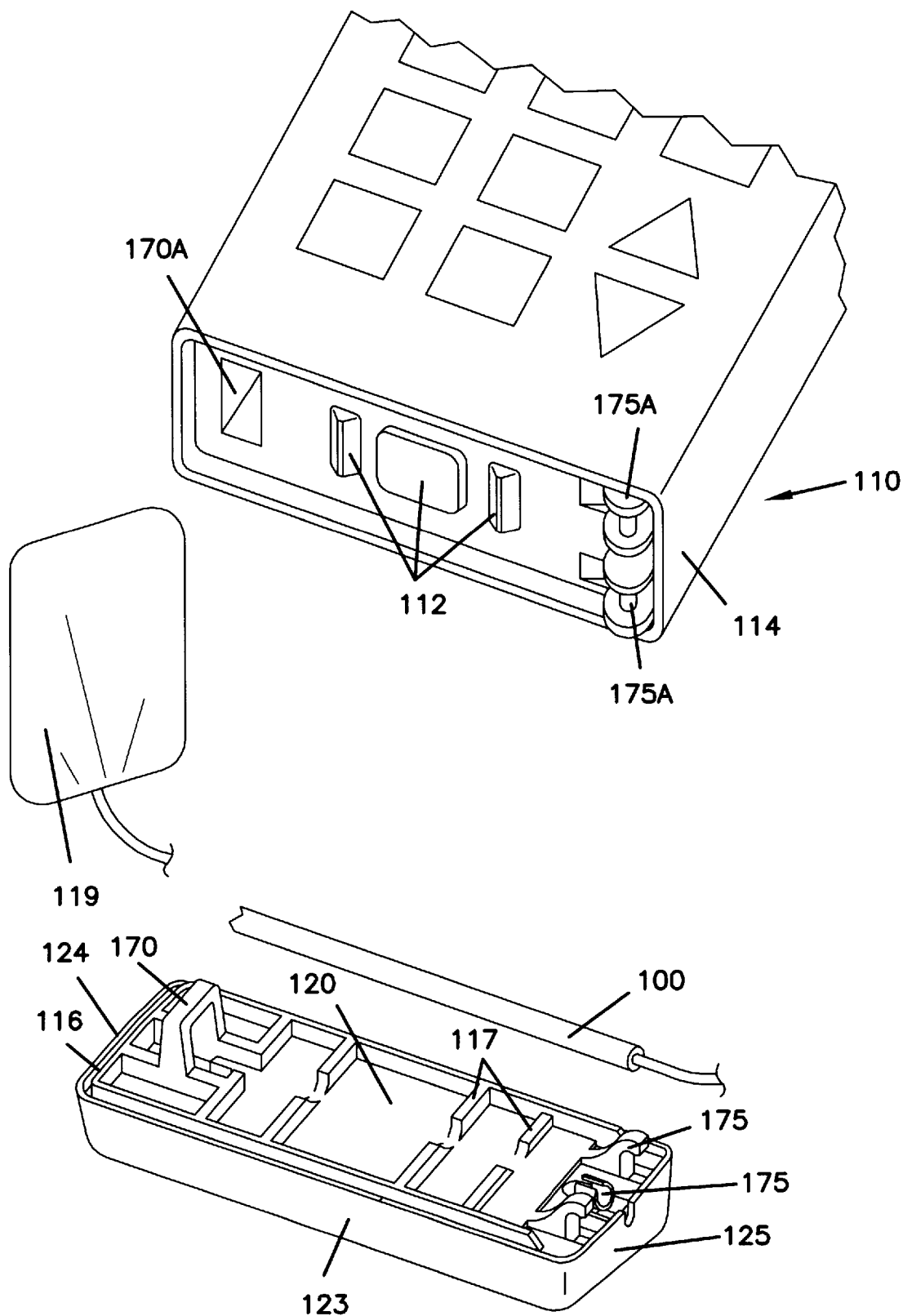
FIG. 1A is a schematic view of an alternative pressure plate with a remote reservoir.

With reference to FIG. 1 there is shown a control module or pump 110 operative in effecting the movement of fluid through a tube 100. For the purposes of illustration, pump 110 includes a body 114 and valves 112. As illustrated, pump 110 is used with a cassette 118 having a pressure plate 120. Pressure plate 120 includes a top and bottom surface, two side walls 123 as well as an upstream wall 124 and a downstream wall 125. Cassette 118 includes a source of fluid contained within a bag 119 or a syringe (not shown). Bag 119 or other fluid reservoir may also be positioned remote from pump 110 and pressure plate 120 as shown in FIG. 1A. Pressure plate 120 includes a plurality of guides 117 positioned on the top of pressure plate 120 which keep tube 100 in place on pressure plate 120. Pressure plate 120 also includes a rail 116 which surrounds pressure plate 120 and engages with body 114 of pump 110.

As illustrated, pressure plate 120 attaches to pump 110 with hooks 175 and loop 170. In particular, hooks 175 engage pins 175A of pump 110, and loop 170 is received within recess 170A. Recess 170A includes a latch (not shown) which selectively engages loop 170 to lock pressure plate 120 to pump 110. When pressure plate 120 is locked to pump 110, tube 100 is continually engaged by at least one of valves 112 such that tube 100 is constantly occluded. When in operation, valves 112 selectively squeeze tube 100 against pressure plate 120 to effect the movement of fluid through tube 100. An example of an expulsor pump is shown in U.S. Pat. No. 4,559,038 to Berg, the specification and drawings of which is herein incorporated by reference. The present invention is directed toward a device which occludes tube 100 when tube 100 becomes disengaged from pump 110. It is to be understood that the present invention may be used with peristaltic pumps, roller pumps, or expulsor pumps.

With reference to FIGS. 2–4, there is shown a first preferred embodiment of the present invention. FIG. 2 illustrates a free-flow protection device 130 which occludes tube 100 from its exterior. Device 130 may be positioned either adjacent to loop 170 or adjacent to hooks 175. Device 130 is preferably attached to one of the guides 117 on the top surface of pressure plate 120. Device 130 includes an elongated bent wire having three legs 132, 134, 136 which operate to selectively occlude tube 100. Device 130 further includes a lever 138 which is deflectable by pump 110, when pressure plate 120 is engaged thereto such that device 130 selectively occludes tube 100.

As best illustrated in FIGS. 3 and 4, each leg includes a first and second end, e.g. leg 132 includes first and second ends 132A and 132B, and leg 134 includes first and second ends 134A and 134B. First leg 132 and third leg 136 are connected between guide 117 so that each end, e.g. 132A and 132B, of each leg is fixed to guide 117. First and third legs 132 and 136 are positioned in a spaced apart relationship with tube 100 passing below first and third legs 132 and 136, respectively. Positioned between first and third legs 132 and 136 is second leg 134 over which tube 100 passes.

Second leg 134 is only attached to guide 117 at one of its ends, preferably its first end 134A. Second end 134B of second leg 134 is attached to lever 138 which projects upwardly and away from the top surface of pressure plate 120.

In a preferred construction, lever 38 includes an engagement member 139 which interfaces with pump 110. Also in its preferred construction, and as illustrated, second end 132B of first leg 132 is connected to second end 136B of third leg 136 by a curved section 133 which is fixed to guide 117 and first end 134A of second leg 134 and first end 136A of third leg 136 are connected by a curved section 135 which is fixed to guide 117 opposite from curved section 133.

First through third legs 132, 134 and 136 are configured so that tube 100 is normally pinched or occluded when lever 138 is in an upward position, as best illustrated in FIG. 4. Tube 100 is held in an occluded condition because second leg 134 acts as a cantilevered spring.

As best illustrated in FIGS. 3 and 4, when pressure plate 120 engages pump 110 lever 138 is deflected downwardly as indicated by arrow A, thereby deflecting second end 134B of second leg 134 downwardly. When second leg 134 is deflected downward, second leg 134 no longer pinches off or occludes tube 100 against first and third legs 132, 136. When engaged to pressure plate 120, lever 138 is deflected downward and device 130 is in a free-flow condition so that fluid can be moved through tube 100 by pump 110. Device 130 may be constructed from a variety of both metallic and non-metallic materials although stainless steel is preferred.

Figure 5:
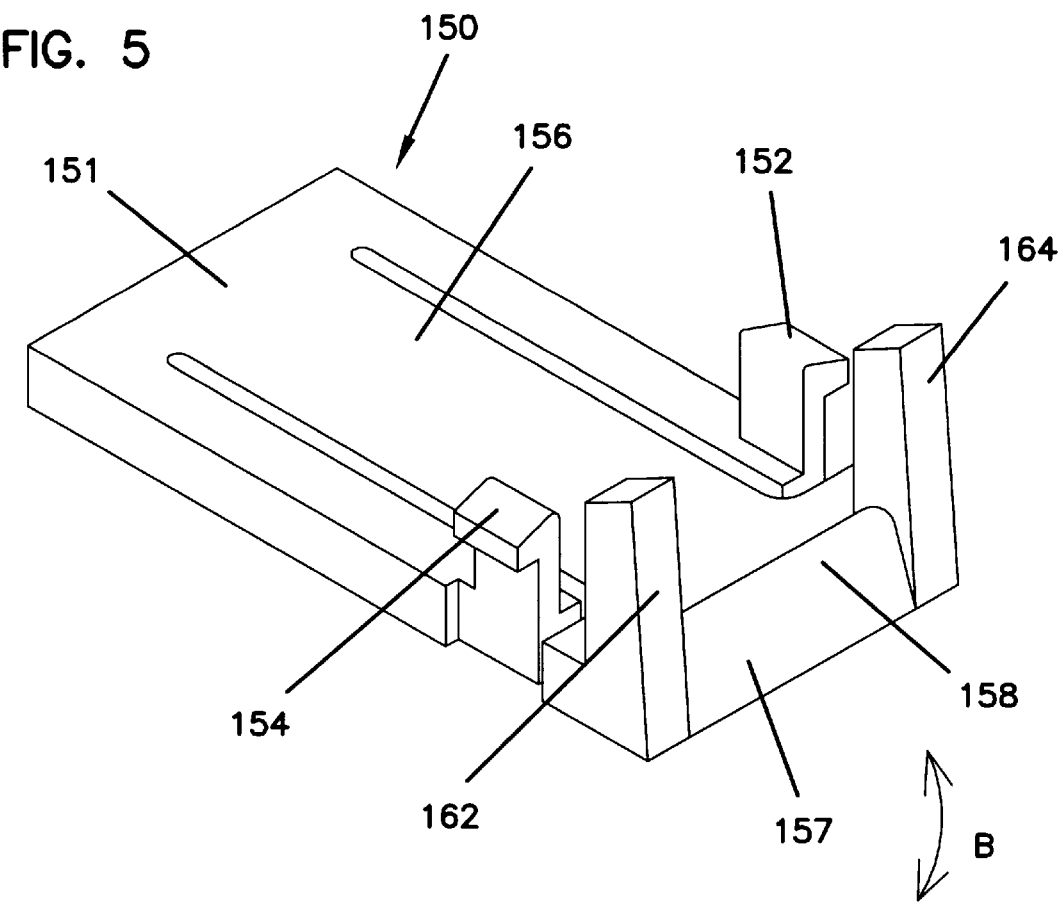
FIG. 5 is a perspective view of a free-flow protection device according to a second preferred embodiment.
Figure 7:
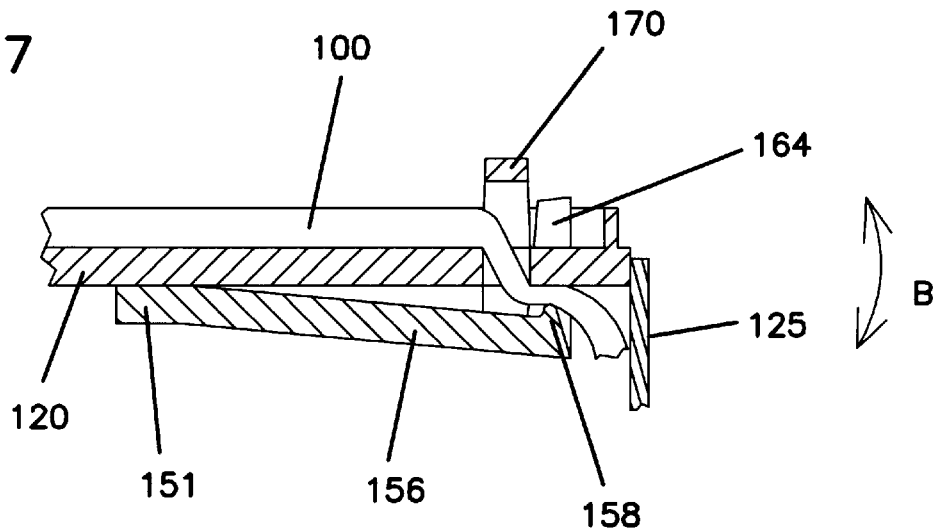
FIG. 7 is a cross-sectional view of the FIG. 6 taken along lines 7—7.
Figure 6:
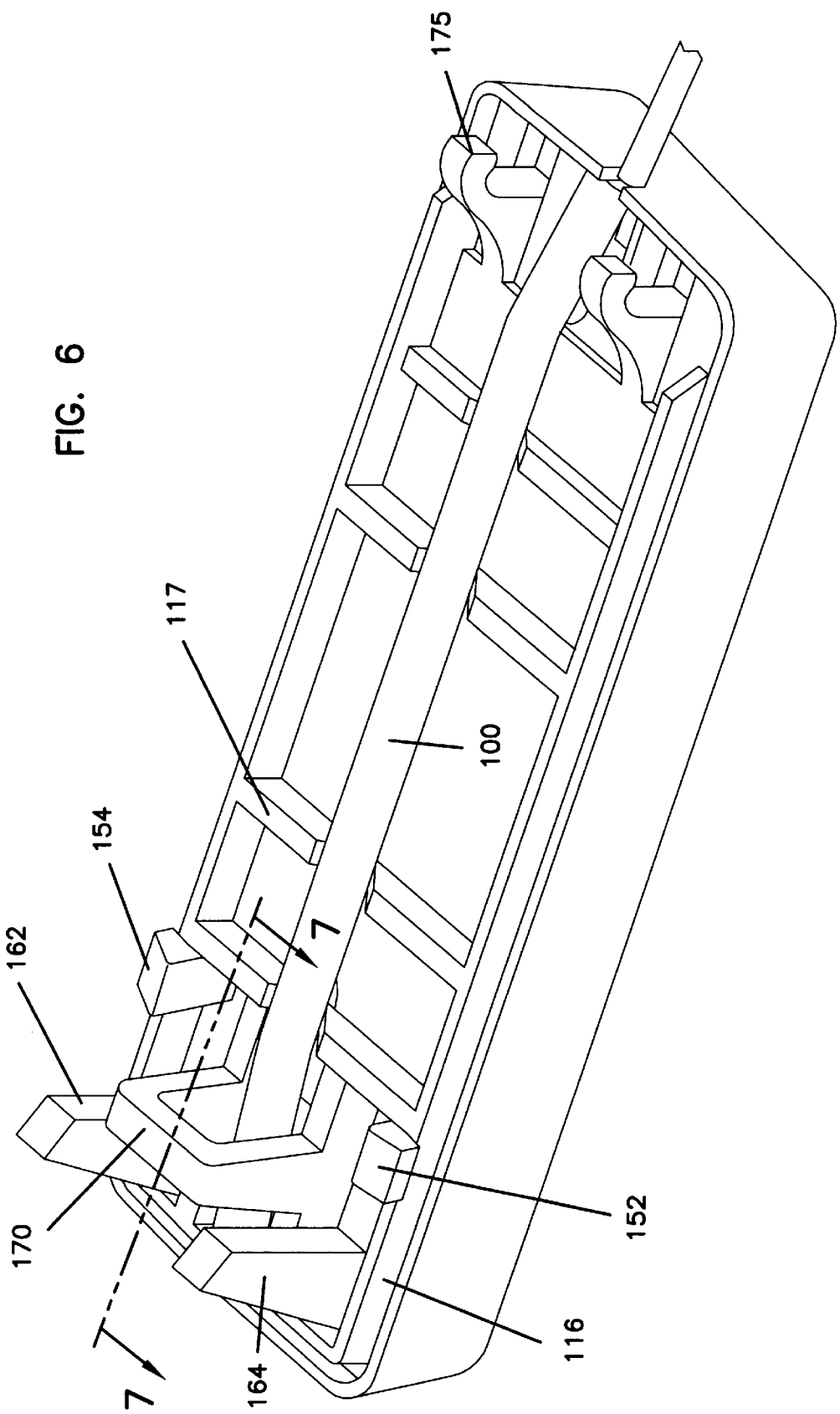
FIG. 6 is a perspective view of the free-flow protection device of FIG. 5 attached to a pressure plate.

With reference to FIGS. 5 through 7 there is shown a second preferred embodiment of the present invention. FIG. 5 illustrates a free-flow protection device 150 for attachment to a pressure plate 120. Device 150 includes a base section 151 which anchors to the bottom of pressure plate 120 by a pair of hooks 152 and 154. As best illustrated in FIG. 6, pressure plate 120 includes a pair of apertures through which hooks 152 and 154 pass so that they may each clip onto rail 116 of pressure plate 120. Alternatively, or in addition, base 151 may be attached to the bottom of pressure plate 120 with adhesives, screws or by other well recognized techniques.

Cantilevered away from base 151 of device 150 is a clamp beam 156. Clamp beam 156 includes a distal end 157 having a clamping portion 158. In the preferred construction of the second embodiment, clamping portion 158 is defined by a raised ridge having a rounded configuration. It is to be understood that configurations other than a raised ridge could be used for the clamping portion. Clamp beam 156 deflects between an occluding position a free flow position as illustrated by arrow B in FIGS. 5 and 7. As best illustrated in FIGS. 6 and 7, clamping portion 158 is positioned below the bottom surface of pressure plate 120 and occludes tube 100 against the bottom surface of pressure plate 120 when beam 156 is in its occluding position. As illustrated, device 150 operates to occlude tube 100 upstream from valves 114. Clamping beam 156 is cantilevered from base 151 to bias clamping portion 158 against the bottom surface of pressure plate 120 so that tube 100 is normally occluded. When deflected from its normal position clamping portion 158 permits a free-flow state within tube 100.

Also attached at the distal end 157 of clamping beam 156 are a pair of spaced apart levers 162 and 164. Levers 162 and 164 are positioned adjacent to clamping portion 158 and extend upwardly and away from clamping portion 158. As shown in FIG. 5, levers 162 and 164 pass through a pair of apertures in pressure plate 120. Levers 162 and 164 extend above engagement loop 170 and are deflected downward by pump 110 when pressure plate 120 is attached to pump 110.

In operation, tube 100 is occluded between the bottom of pressure plate 120 and clamping portion 158 until pressure plate 120 is attached to pump 110. Pump 110 forces levers 162 and 164 downward against the force of clamping beam 156. As levers 162 and 164 are forced downward, clamping portion 158 is pushed away from the bottom of pressure plate 120, thereby placing tube 100 into a free-flow condition. If pressure plate 120 becomes disengaged from pump 110, clamping beam 156 will force clamping portion 158 upward to occlude tube 100 against the bottom surface of pressure plate 120.

The device illustrated in FIGS. 5 through 7 may be constructed from either metal or plastic and has the advantage that it is easily manufactured. Device 150 may be attached to pressure plate 120 either when the pressure plate 120 is manufactured or it may be added later. Device may 150 may also be integrally formed with pressure plate 120. Device 150 is advantageous in that it is minimally obtrusive to tube 100 and pressure plate 120.

Figure 9:
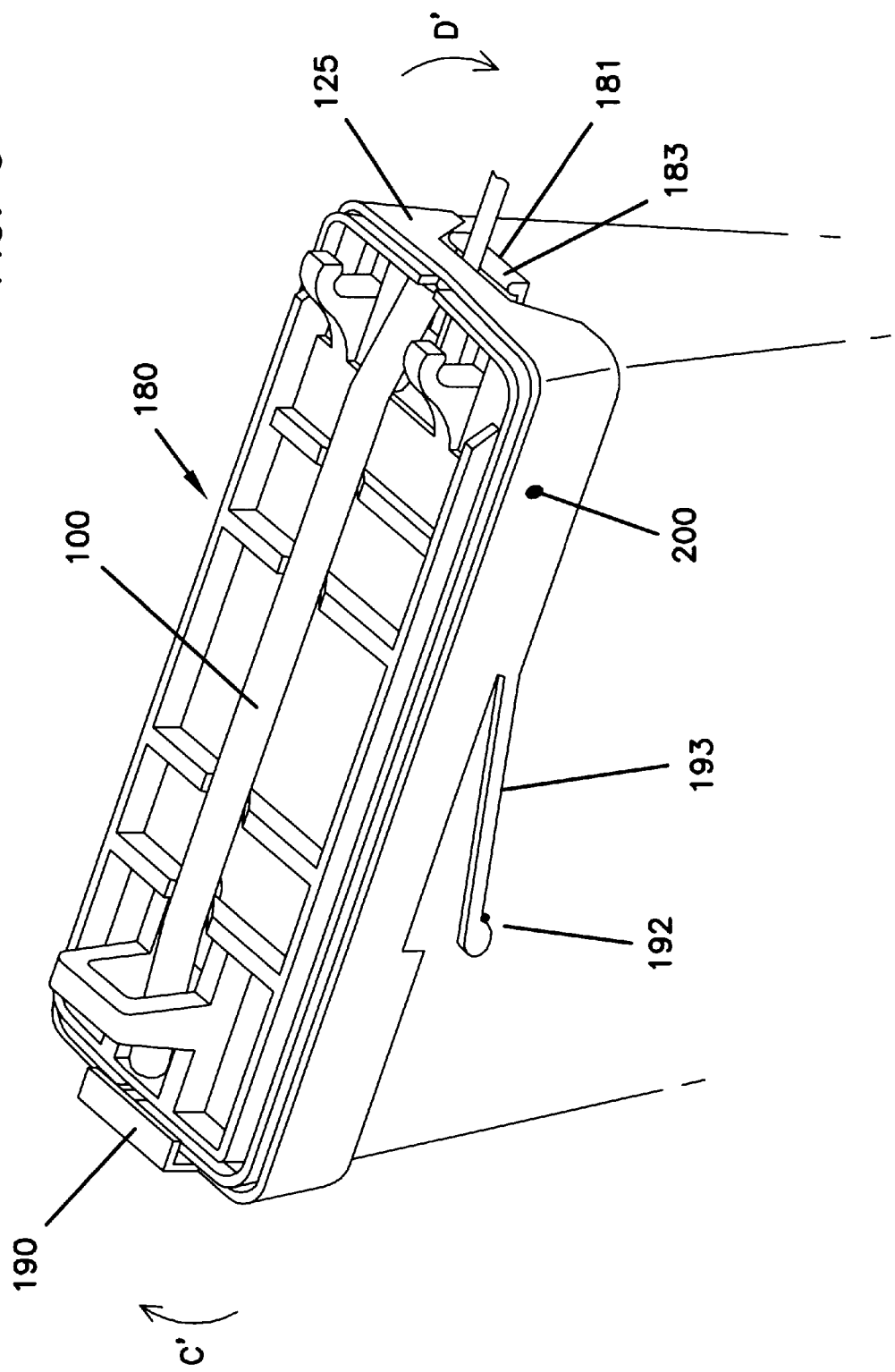
FIG. 9 is a perspective view of the free-flow protection device and the pressure plate of FIG. 8 showing the tube in a occluded state.
Figure 10:
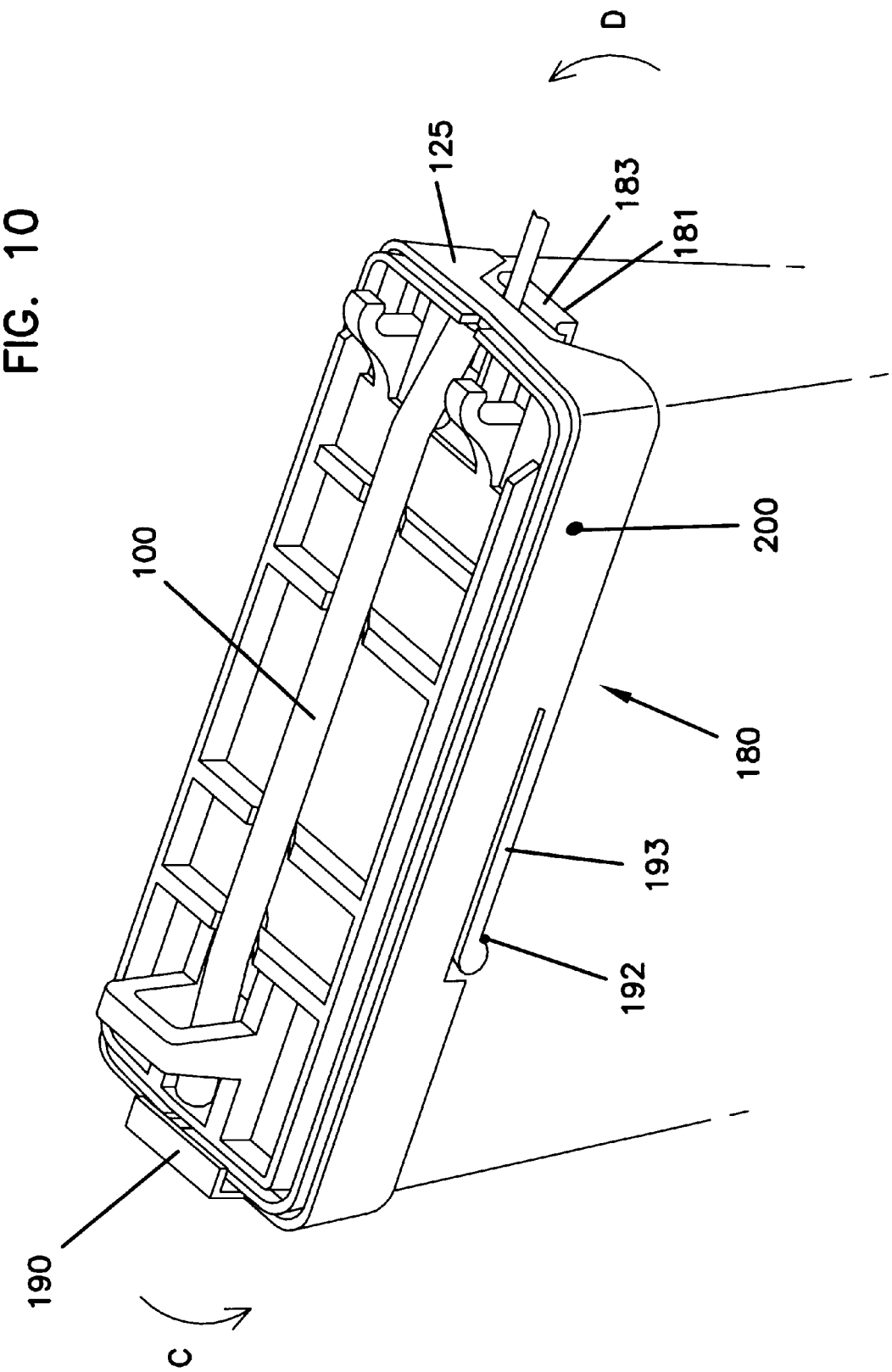
FIG. 10 is a perspective view of the free-flow protection device of FIG. 8 showing the tube in a free-flow state.

FIGS. 8–10 show a third preferred embodiment of a free-flow protection device 180. As shown, device 180 occludes tube 100 downstream from pump 110. Device 180 occludes tube 100 against a fixed extension 181 of pressure plate 120 which extends from downstream wall 125, although it is recognized that extension 181 may be placed on either upstream wall 124 or downstream wall 125 of pressure plate 120. Extension 181 also includes a raised ridge 183 against which tube 100 is occluded.

As best illustrated in FIG. 8, device 180 is fitted around pressure plate 120 such that it encircles pressure plate 120. Device 180 includes upstream and downstream walls 182A and 182 and two side walls 184 and 184A. Side walls 184 and 184A are identical to one another. Downstream wall 182 includes a cut out which forms a clamping portion 185 operative to occlude tube 100 against raised ridge 183 of extension 181. As illustrated, and opposite from clamping portion 185, device 180 includes a lever 190 positioned on upstream wall 182. Lever 190 projects upward and away from pressure plate 120 for engagement with pump 110. Clamping portion 185 on downstream wall 182 of device 180 is operative in occluding tube 100 against raised ridge 183 of extension 181.

Device 180 is pivotably supported around pressure plate 120 by a pair of pins 200 positioned on opposite side walls 123 of pressure plate 120. Clamping portion 185 of downstream wall 182 is biased toward raised ridge 183 by a pair of cantilevered springs 193 an 194 positioned on side walls 184 and 184A of device 180. Cantilevered springs 193 and 194 are fixed against a second pair of pins 192 on side walls 123 of pressure plate 120. Cantilevered springs 193 and 194 operate to bias clamping portion 185 pivotably downward and against raised ridge 183 of extension 181 of pressure plate 120 to pinch tube 100.

When pressure plate 120 is attached to pump 110, pump 110 forces lever 190 downward as shown by arrow C in FIG. 10. In response to the downward movement of lever 190 device 180 pivots about pins 200, against the force of cantilevered springs 193, and 194, thereby moving clamping portion 185 upwardly away from raised ridge 183 as shown by arrow D in FIG. 10. If pressure plate 120 becomes disengaged from pump 110, lever 190 will be forced upward by cantilevered springs 193 and 194, as shown by arrow C in FIG. 9, which will force clamping portion 185 downward toward raised ridge 183 as shown by arrow D in FIG. 9. Releasing pressure plate 120 from control module 110 will thus result in tube 100 being occluded between clamping portion 185 and raised ridge 183 of extension 181.

Device 180 may be constructed from plastic or metal or a combination of both. For example, cantilevered springs 193 and 194 may be constructed from stainless steel while the remainder of device 180 may be constructed from plastic. Device 180 provides advantages in manufacturing and packaging. For example, device 180 will riot interfere with the area surrounding guides 117 or tube 100 thereby permitting other devices to be attached to pressure plate 120 without difficulty. For example, various transducers may be attached to tube 100 which may be used to determine the status of fluid flow through tube 100. These transducers may detect occlusions, or bubbles within the fluid flow for example. Device 180 may also be constructed in a single molding operation to decrease the cost of manufacture.

FIGS. 11–13 illustrate a fourth preferred embodiment of a free-flow protection device 210 including a clamping door 220 operative in selectively occluding tube 100 against the downstream or upstream wall 125 or 124 of pressure plate 120 when pressure plate 120 becomes disengaged from pump 110. In addition to clamping door 220, device 210 includes a lever 224, a spring 230 and a rotatable shaft 228. Clamping door 220 preferably is attached adjacent to downstream wall 125 of pressure plate 120, although it is understood that clamping door 220 may be attached adjacent upstream wall 124. As shown in FIG. 13, clamping door 220 is generally U-shaped, having opposed side walls 222 and 223 and a connecting wall 225. As illustrated in FIGS. 11 and 12, clamping door 220 surrounds the exterior of pressure plate 120 adjacent downstream wall 125. Connecting wall 225 of clamping door 220 includes a clamping portion 227 preferably configured as a raised ridge. As shown, clamping portion 227 is positioned below the top surface of pressure plate 120. Clamping door 220 also includes a pair of spaced apertures 214 and 215 positioned on its opposed walls 222 and 223. Apertures 214, 215 preferably are keyed as to rigidly hold shaft 228, and in the illustrated embodiment have a rectangular configuration.

Lever 224 is preferably located below the top surface of pressure plate 120. As illustrated in FIGS. 11–13, pressure plate 120 includes a cassette 118 which receives a bag of fluid. As shown in FIG. 11, lever 224 is located below pressure plate 120 within cassette 118. Lever 224 includes a first end 232 connected to clamping door 220 and a second end 234 operable in being deflected by pump 110. Second end 234 of lever 224 includes an upward extension 235 which protrudes through a slot 238 in the top surface of pressure plate 120 proximate to upstream wall 124. Lever 224 is connected to clamping door 220 by shaft 228. Shaft 228 is rigidly fixed perpendicularly to first end 232 of lever 224. Shaft 228 passes through a pair of holes 218 and 219 positioned on side walls 123 of pressure plate 120.

Shaft 228 includes a pair of keyed end sections 240 and 242 which are configured to engage keyed apertures 214 and 215 on clamping door 220. Keyed end sections 240, 242 rigidly mate with clamping door 220 through keyed apertures 214 and 215 so that clamping door 220 rotates in response to rotation of shaft 228. When clamping door 220 rotates, clamping portion 227 occludes tube 100 against downstream wall 125 of pressure plate 120. Positioned around shaft 228 is a coiled spring 230 having a top leg 252 and a side leg 254 preferably spaced approximately ninety degrees apart. In the preferred embodiment, top leg 252 is fixed to lever 228 and side leg 254 is fixed to the inner surface of downstream edge 125 of pressure plate 120 or cassette 118. Spring 230 operates to bias lever 228 to an upward position such that extension 235 projects through slot 238 in pressure plate 120. Spring 230 also biases shaft 228 so that clamping portion 227 occludes tube 100 against downstream wall 125.

In operation, when pressure plate 120 is engaged to pump 110 extension 235 of lever 228 is pushed down through slot 238 in pressure plate 120. When extension 235 is pushed through slot 238, shaft 228 rotates against the force of coil spring 230 which rotates clamping door 220 and thus clamping portion 227 away from tube 100 so that a free-flow condition is present when pump 110 is engaged to pressure plate 120. When pressure plate 120 disengages from pump 110, coiled spring 230 biases lever 224 upward and clamping door 220 and clamping portion 227 move toward tube 100 so that clamping portion 227 occludes tube 100.

Device 210 provides advantages in that it utilizes a separate coil spring 230. Coil spring 230 has a longer operational life than other types of springs, such as cantilevered springs. Further, device 210, like other preferred embodiments, is unobtrusive to the top of pressure plate 120 so that other features may be included on pressure plate 120, such as transducers operate to detect occlusions or bubbles within tube 100.

Figure 15:
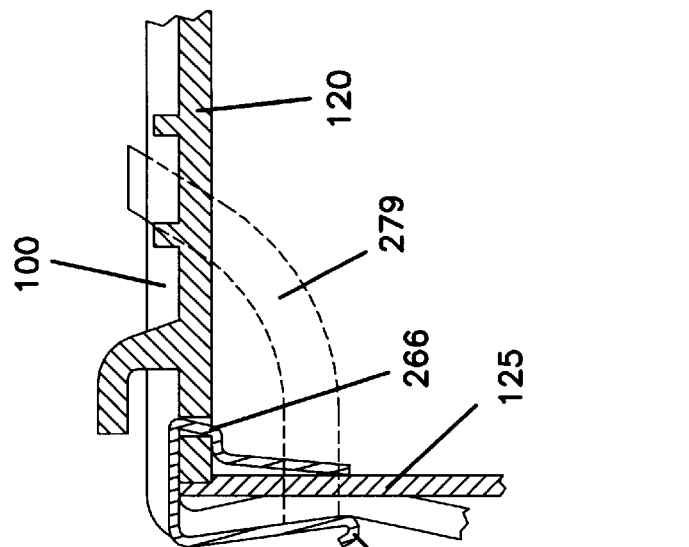
FIG. 15 is a cross-sectional view of the free-flow protection device and pressure plate of FIG. 14.
Figure 14:
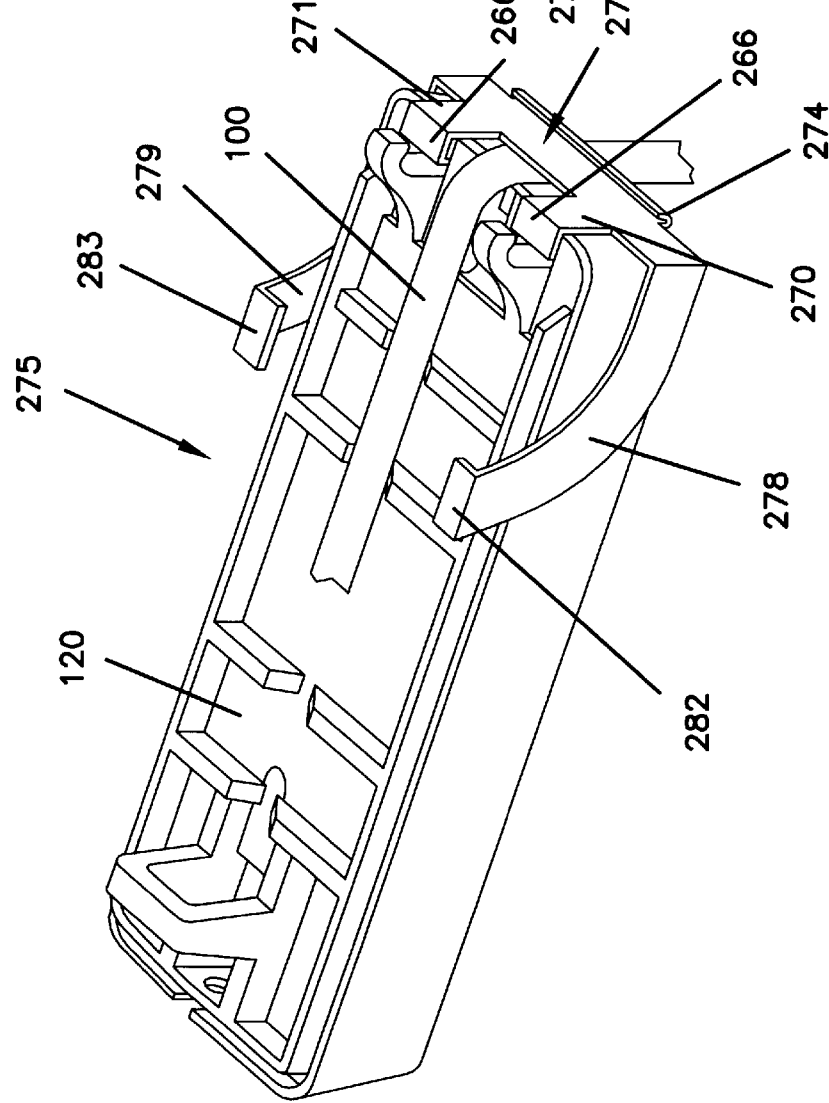
FIG. 14 is a perspective view of a free-flow protection device and a pressure plate according to a fifth preferred embodiment.

Now with reference to FIGS. 14 and 15, there is shown a fifth preferred embodiment of a free-flow protection device 275 which occludes tube 100 against either the upstream or downstream wall 124 or 125 of pressure plate 120. As shown in FIG. 14, device 275 is configured to occlude tube 100 against downstream wall 125 of pressure plate 120. Device 275 is anchored to the top surface of pressure plate 120 by a pair of hooks 266 attached adjacent downstream wall 125. In particular, and as shown in FIG. 15, hooks 266 extend around downstream wall 125 such that hooks 266 rigidly fix device 275 to pressure plate 120. Device 275 also includes a clamping portion 272 operative in occluding tube 100. Clamping portion 272 is attached to hooks by a pair of spaced legs 270 and 271 which extend from hooks 266 down the outer surface of downstream wall 125. Clamping portion 272 preferably includes a raised ridge. Extending along the periphery of pressure plate 120 along the opposed side walls 123 of pressure plate 120 are a pair of levers 278 and 279. Levers 278 and 279 are preferably semicircular in shape and extend from clamping portion 272 to a location above top surface of pressure plate 120. In the illustrated embodiment, levers 278 and 279 each include flat engagement surfaces 282, 283 for engagement with pump 110 when pressure plate 120 is attached thereto.

Tube 100 passes between the downstream wall 125 of pressure plate 120 and the raised ridge of clamping portion 272. Spaced arms 270 and 271 of device 275 bias clamping portion 272 toward downstream wall 125 of pressure plate 120 such that when pressure plate 120 is not engaged to pump 110, the raised ridge of clamping portion 272 pinches off tube 100 against downstream wall 125 of pressure plate 120 such that tube 100 is occluded. Legs 270 and 271 bias clamping portion 272 toward tube 100 and generate the appropriate amount of force to keep tube 100 occluded when pump 110 is not attached to pressure plate 120.

When pressure plate 120 is attached to pump 110, levers 278 and 279 are forced downward, thereby pushing the raised ridge of clamping portion 272 away from tube 100 against the force of legs 270 and 271 which creates a free-flow condition. When pressure plate 120 disengages from pump 110, legs 270 and 271 force the raised ridge of clamping portion 272 against tube 100 to occlude tube.

Device 275 may be constructed from either plastic or metal. Device 275 requires very little materials to manufacture and therefore is inexpensive. Device 275 also is advantageous in that is does not interfere with the top surface of pressure plate 120.

FIGS. 16–19 illustrate a sixth preferred embodiment of a free-flow protection device 300 which is attached around the pressure plate 120. As shown in FIG. 16, device 300 generally is rectangular in configuration and is adapted to surround pressure plate 120. Device 300 includes two side walls 301 and 303 and a downstream wall 307 and an upstream wall 305. As illustrated, device 300 includes a spring 312 positioned at one of its corners. To place device 300 around pressure plate 120, three hooks 302, 304 and 306 are latched to the top surface of pressure plate 120. Device 300 also attaches to pressure plate at a pivot point 318 located at side wall 303. Pivot point 318 can include a pin positioned on side wall 123 of pressure plate 120 which fits over a hole in side wall 303 of device 300.

Device 300 includes a locking clamp 310 positioned adjacent spring 312 and parallel to side wall 303. Clamp 310 pivots toward and away from side wall 303 such that when pivoted toward side wall 303, device 300 is rigidly attached to pressure plate 120 by hooks 302, 304 and 306. Downstream wall 307 of device 300 acts as a clamping portion and includes a raised ridge 320 on its lower edge so that tube 100 passes between raised ridge 320 and downstream wall 125 of pressure plate 120. When locking clamp 310 is rotated to lock device 300 around pressure plate 120, spring 312 also biases raised ridge 320 against tube 100 as to occlude tube 100.

Device 300 includes a lever 308 positioned on side wall 303 of device 300. When pressure plate 120 and device 300 are attached to pump 110, lever 308 is forced downward. As lever 308 is forced downward, device 300 rotates about pivot 318 such that device 300 twists and forces raised ridge 320 away from tube 100 so that fluid may pass freely therethrough.

It is recognized that device 300 may be constructed from metal, plastic or a combination of the two. Preferably, spring 312 is constructed from metal. Device 300 provides the advantage of being able to be attached to an existing pressure plate without significant modifications to the pressure plate 120.

As shown in FIGS. 20–27, further preferred embodiments of the present invention are each configured to be placed within the lumen of tube 100 as opposed to the embodiments shown in FIGS. 2–19.

Figure 20:
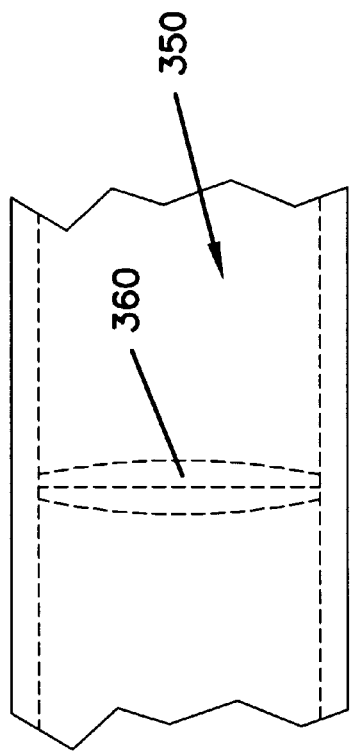
FIG. 20 is a side view of a tube including a free-flow protection device according to a seventh preferred embodiment, showing the tube in an occluded state.
Figure 22:
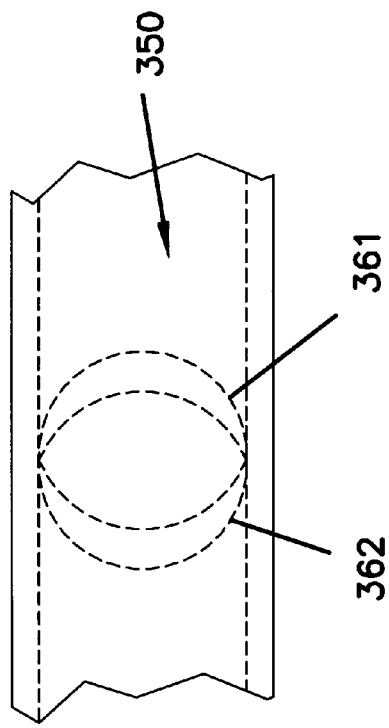
FIG. 22 is a side view of the tube and free-flow protection device of FIG. 20 showing the tube as compressed and in a free-flow state.
Figure 21:
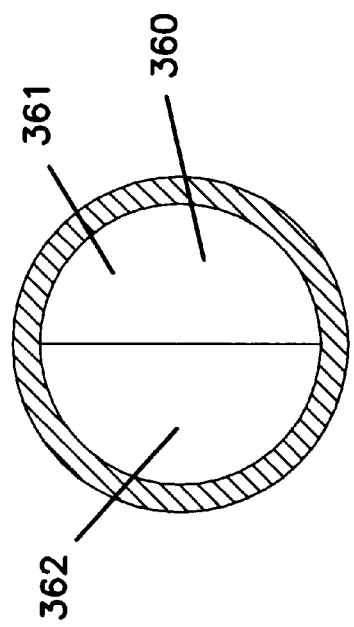
FIG. 21 is an end view of the tube and the free-flow protection device of FIG. 20.
Figure 23:
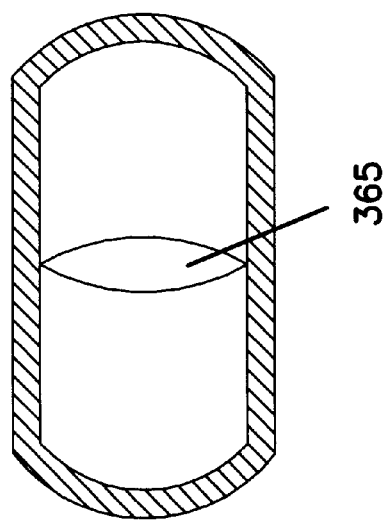
FIG. 23 is an end view of the free-flow protection device and tube of FIG. 22.
Figure 24:
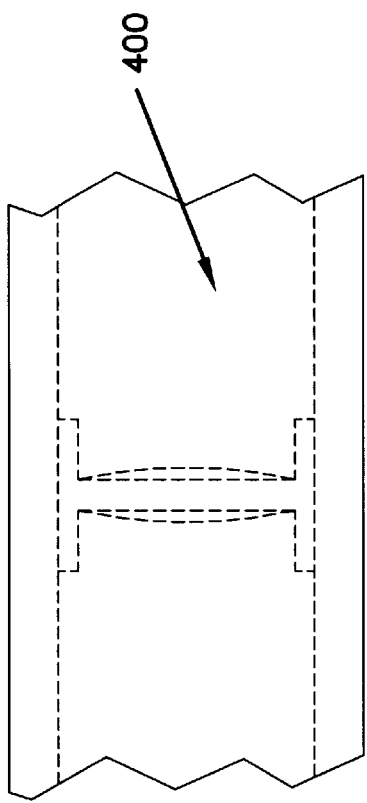
FIG. 24 is a side view of a tube including a free-flow protection device according to an eighth preferred embodiment, showing the tube in an occluded state.

FIGS. 20–23 illustrate a free-flow protection device 350 according to a seventh preferred embodiment. FIGS. 20 and 21 illustrate device 350 positioned within tube 100. Device 350 is a slit valve 360 which is positioned within tube 100 such that it is adjacent both pressure plate 120 and pump 110. As shown in FIG. 21, when tube 100 is in its normal condition, slit valve 360 is closed. Slit valve 360 is comprised of two semi-circular sections 361, 362. As shown in FIGS. 22 and 23, when tube 100 is compressed, as when it is attached to pump 110, sections 361 and 362 separate thereby defining and opening 365 through which fluid will pass.

Figure 26:
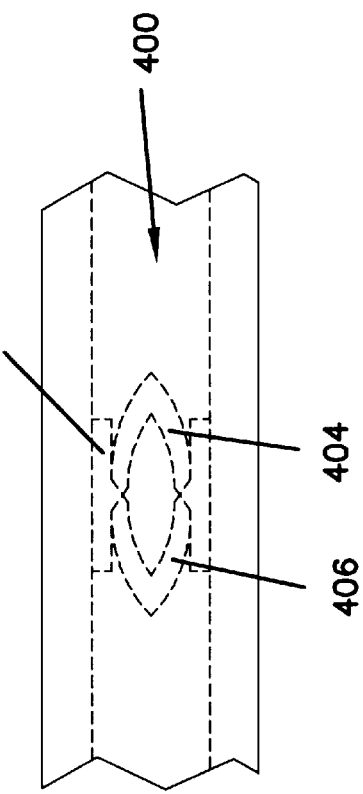
FIG. 26 is a side view of the tube and free-flow protection device of FIG. 24 showing the tube as compressed and in a free-flow state.
Figure 25:
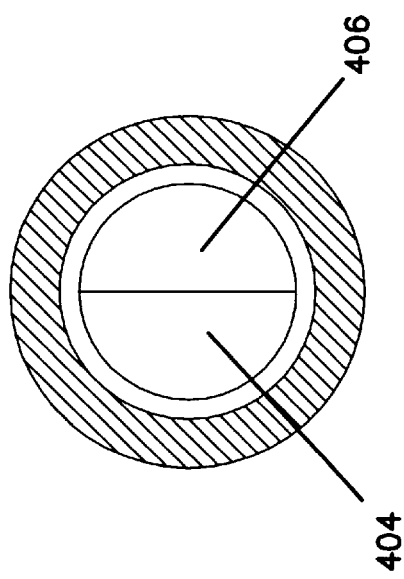
FIG. 25 is a end view of the tube and free-flow protection device of FIG. 24.
Figure 27:
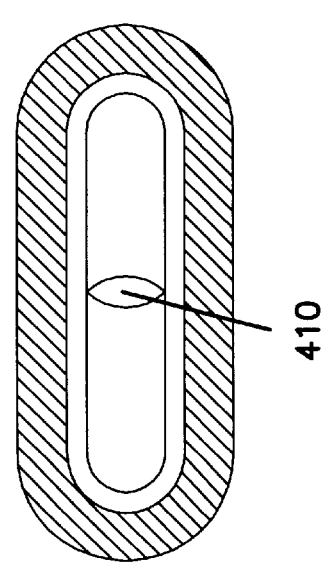
FIG. 27 is a end view of the free-flow protection device and tube of FIG. 26.

FIGS. 24–27 illustrate an eighth preferred embodiment of a free-flow protection device including a slit valve 400. Slit valve 400 includes an inner support 402 and two semi-circular sections 404 and 406 positioned between inner support 402. When tube 100 is compressed, as shown in FIGS. 26 and 27, sections 404 and 406 separate to define an opening 410 through which fluid may pass.

Because the in-line valves of the seventh and eighth preferred embodiments operate in response to tube 100 being compressed they do not affect the volume of fluid delivered, as do some prior art in line fluid devices. Also, the structure is internal to the tube so no external structure is used in the embodiments of FIGS. 2–19.

Further, it is to be understood that: even though numerous characteristics and advantages of the invention have been set forth in the foregoing description, together with details of the structure and function of the invention, the disclosure is illustrative only and changes may be made in detail, and especially in matters of shape, size and arrangement of parts wherein the principles of the invention the full extent indicated by the broad general meaning of the terms in which the pendent claims are expressed.

What is claimed is:

1. A cassette for attachment to a pump, the cassette enclosing a reservoir of fluid with a tube extending from the reservoir, the cassette comprising:

a pressure plate on which the tube is attached, the pressure plate being selectively attachable to the pump so that when the tube and pressure plate are attached to the pump the pump effects movement of fluid through the tube; and a free-flow protection device responsive to the pressure plate being engaged to the pump to move the free-flow protection device from a tube occluding state to a free-flow state, wherein the free-flow protection device is internal to the tube.

2. A free-flow protection device for occluding a tube when the tube disengages from a pump, the tube connectable to the pump by a pressure plate so that the pump effects movement of fluid through the tube, the free-flow protection device comprising:

a lever deflectable between a first position and a second position such that when the pressure plate is disengaged to the pump the lever is in the first position and when the pressure plate is engaged from the pump the lever is in the second position; and a clamping portion movable between an occluding position and a free-flow position, the clamping portion connected to the lever so that when the lever is in the first position the clamping portion is in the occluding position, and when the lever is in the second position the clamping portion is in the free-flow position, wherein the clamping portion is biased towards its first position, and further comprising a beam including a first end anchored to the pressure plate and a second end which includes the clamping portion, the clamping portion normally occluding the tube against the pressure plate and the lever operative in deflecting the beam and the clamping portion away from the tube when the lever moves from its first position to second position to create a free-flow condition, wherein the beam is anchored to the pressure plate with at least one hook.

3. A free-flow protection device as in claim 2 wherein the lever extends through an aperture in the pressure plate.

4. A free-flow protection device for occluding a tube when the tube disengages from a pump, the tube connectable to the pump by a pressure plate so that the pump effects movement of fluid through the tube, the free-flow protection device comprising:

a lever deflectable between a first position and a second position such that when the pressure plate is disengaged to the pump the lever is in the first position and when the pressure plate is engaged from the pump the lever is in the second position;

a clamping portion movable between an occluding position and a free-flow position, the clamping portion connected to the lever so that when the lever is in the first position the clamping portion is in the occluding position, and when the lever is in the second position the clamping portion is in the free-flow position;

a clamping door which includes the clamping portion, the clamping door rotatable in response to the lever moving from its second position to its first position to force the clamping portion against the tube.

5. A free-flow protection device for use in occluding a tube when the tube disengages from a pump, the tube being connectable to the pump so that the pump effects fluid movement through the tube, the device comprising:

a tube including a lumen and a longitudinal axis;

a valve positioned within the lumen of the tube, the valve occluding the lumen of the tube when the tube is not compressed by the pump in a direction transverse to the longitudinal axis; and a pressure plate mounted to the tube for holding the tube adjacent to the pump.

6. A free-flow protection device as in claim 5 wherein the valve includes at least two semi-circular sections which cooperate to occlude the tube when the tube is not compressed and define an aperture when the tube is compressed.

7. A free-flow protection device as in claim 6 wherein the semi-circular sections are connected to the lumen of the tube with an anchor section.

8. A method of pumping a fluid through a tube comprising:

providing a pump;

engaging the tube to the pump so that the pump effects movement of fluid through the tube, wherein the pump opens a free flow protection device, wherein the free-flow device is positioned within the tube, wherein the pump opens the free-flow protection device by compressing the tube in a direction transverse to a longitudinal axis of the tube; and occluding the tube with the free flow protection device when the tube disengages from the pump.

9. A fluid delivery device for effecting the movements of fluid through a lumen of a tube, the device comprising:

a pump engaged to a tube for affecting the movement of fluid through the tube; and means for occluding the tube when the tube disengages from the pump, wherein the means for occluding the tube is positioned within the lumen of the tube, wherein the means for occluding no longer occludes the tube when the tube is compressed by the pump in a direction transverse to a longitudinal axis of the tube.

10. A fluid delivery device as in claim 9 wherein the tube is attached to a pressure plate and the pressure plate is attached to the pump.

11. A cassette for attachment to a pump, the cassette comprising:

a tube;

a pressure plate on which the tube is attached, the pressure plate being selectively attachable to the pump so that when the tube and pressure plate are attached to the pump the pump effects movement of fluid through the tube; and a free-flow protection device responsive to the pressure plate being engaged to the pump to move the free-flow protection device from a tube occluding state to a free-flow state, wherein the free-flow protection device is internal to the tube.

* * * * *